United States Patent [19]

O'Lenick, Jr.

[11] Patent Number: 5,149,765

[45] Date of Patent: Sep. 22, 1992

[54] TERMINAL PHOSPHATED SILICONE POLYMERS

[75] Inventor: Anthony J. O'Lenick, Jr., Lilburn, Ga.

[73] Assignee: Siltech Inc., Norcross, Ga.

[21] Appl. No.: 778,506

[22] Filed: Oct. 17, 1991

Related U.S. Application Data

[63] Continuation-in-part of Ser. No. 546,358, Jun. 27, 1990, Pat. No. 5,070,171.

[51] Int. Cl.$^5$ ............................................. C08G 77/04
[52] U.S. Cl. ...................................... 528/25; 528/30; 528/33; 525/474
[58] Field of Search ................. 525/474; 528/30, 33, 528/25

[56] References Cited

U.S. PATENT DOCUMENTS

| | | | |
|---|---|---|---|
| 3,385,914 | 5/1968 | Hindersinn et al. | 528/30 |
| 4,629,602 | 12/1986 | Gousetis et al. | 528/30 |
| 5,070,168 | 12/1991 | O'Lenick, Jr. | 525/474 |

*Primary Examiner*—Melvyn I. Marquis
*Assistant Examiner*—Karen A. Hellender

[57] ABSTRACT

The invention relates to a series of novel organofunctional silicone polymers which have a phosphate terminal functionality present within the polymer. Compounds of the invention, by virtue of their phosphate group, provide a nonvolatile lubricant antistat which can be applied to a variety of fibers. The compounds of the invention deposit on the fiber surface thereby altering the surface's physical properties. Compounds of the present invention by virtue of their linear nature are film formers on a variety of substrates, including hair and skin.

The compounds of the present invention are prepared by phosphation of a hydroxyl group on the silicone polymer. The compounds useful as raw materials are terminal dimethicone copolyols. The introduction of a phosphate group onto the silicone polymer is achieved by reaction of the hydroxyl group on the silicone with a suitable phosphating reagent. Another method of introducing the phosphate group is by the phosphation of the hydroxy containing vinyl intermediate which is subsequently reacted with the silicone polymer by hydrosilation.

6 Claims, No Drawings

TERMINAL PHOSPHATED SILICONE POLYMERS

RELATED APPLICATIONS

This application is a continuation in part of co-pending application Ser. No. 07/546,358, filed Jun. 27, 1990, now U.S. Pat. No. 5,070,171.

BACKGROUND OF THE INVENTION

FIELD OF INVENTION

The present invention relates to a series of novel phosphated silicone polymers which are substantive to fiber and provide antistatic properties to various fibers. The compounds, because they contain a pendant ionizable phosphate group provide the desired antistatic and lubrication properties to the fiber. Since the compounds of the present invention are high molecular weight silicone polymers, they have a high degree of oxidative stability, even at elevated temperatures. In addition, these compounds are non volatile. This combination of properties makes these polymers ideally suited for use as fiber lubricants/antistats. The compounds of the present invention are also stable to alkaline solutions, unlike the hydroxy containing silicone polymers from which they are made.

The compounds of the present invention are prepared by the phosphation of a terminal hydroxyl group which is present on a silicone polymer. In a preferred embodiment the hydroxy containing silicone polymer has been alkoxylated with ethylene oxide, propylene oxide, butylene oxide or mixtures thereof. The ability to regulate the type of alkylene oxide and amount present in the silicone polymer results in a series of products ranging in water solubility. The technology used to produce the compounds of the present invention is very flexible and allows us to prepare performance tailored molecules for specific applications.

This application is a continuation in part of co-pending application Ser. No. 07/546,358 filed Jun. 27, 1990, now U.S. Pat. No. 5,070,171. Unlike the compounds of the referenced application, these products are linear and were found to produce elastomeric films on a variety of substrates. The films are hydrophobic, but allow air to pass through them. In other words they are permeable to air but impermeable to higher molecular weight materials like water. This property makes these materials more substantive and useful in personal care applications like the formulation of sun screens.

OBJECT OF THE INVENTION

It is the object of the present invention to provide a series of novel phosphated silicone polymers, which have the phosphate group in the terminal position. These materials are substantive to the surface of a fibers. This substantivity results in antistatic properties and lubricity. The superior antistatic properties of the compounds of the present invention are an important benefit, since this is a major aspect of fiber lubrication.

It is another objective of the current invention to provide terminal phosphated silicone polymers which have very low volatility. Volatility is a major concern in formulating fiber lubricants. This is due to the fact that fiber lubricants are exposed to high temperatures during processing. Volatile lubricants, like non-silicone based phosphate esters, evaporate from the fiber and go into the air. This results not only in loss of efficiency and high costs, but potential environmental contamination in the workplace.

Still another object of the present invention is to provide a series of terminal phosphated silicone polymers which have differing solubilities in water and organic solvents. This is achieved by selection of the hydroxy silicone polymer used as a raw material.

Application of the compounds of the invention can be from solvent, aqueous dispersion or solution, or applied neat in these processes.

The silicone polymers, suitable as raw materials, in a preferred embodiment, contain varying amounts of ethylene oxide, propylene oxide or butylene oxide or mixtures thereof. The presence of the oxide in the phosphated silicone polymer results in compounds with an inverse cloud point. Inverse cloud point phenomenon are well known to those skilled in the art of nonionic surface active agents. The inverse cloud point is defined as a temperature above which the polymer has minimal solubility in water. If heat is applied to an aqueous solution of the nonionic at the inverse cloud point the material will become insoluble, and the solution will turn milky. It is at this point that the polymer has minimal water solubility. Since the product is no longer in solution at above this temperature, it is within this temperature range that the product has maximum substantivity to a fiber. The ability to use temperature to deposit a lubricant, antistat onto a fiber offers a great advantage in cost effectiveness of fiber treatment, and results in less product usage.

DESCRIPTION OF THE ARTS AND PRACTICES

Silicone oils (dimthylpolysiloxane) have been known to be active at the surface of plastic, cellulosic and synthetic fibers as well as paper. Despite the fact that they are lubricants that are stable to oxidation, their high cost and lack of durability has made them cost prohibitive in most application areas. Silicone oils need to be emulsified prior to application. This requires high pressure equipment, surface active agents and generally results in a milky emulsion. Emulsions have experienced stability problems both in terms of freeze thaw instability and upon heating. This has resulted in minimal acceptance of them in commercial products.

The low efficiency of silicone oils is due to the fact that the oil is very water insoluble. Emulsions are generally prepared which contain silicone dispersed in micelles. While this method of application is easier for processing, much of the oil stays in the surfactant micelle and never gets deposited on the fiber. That which does deposit on the fiber surface remains there by hydrophobic binding, not ionic bonding. Since the polydimethylsiloxane is not chemically bonded the effect is very transient. The product is removed with one washing.

Fatty alcohol phosphate esters have been known fiber lubricants for many years. They have a much lower molecular weight than the silicone based compounds of the present invention. For this reason, they are much more volatile and cannot be used in high temperature fiber applications. The standard fatty phosphate esters used in fiber lubricant formulations, are not as efficient as those based upon silicone polymers.

Many attempts have been made to overcome these problems and get a truly substantive non volatile product, which deposits on fiber efficiently. One approach has been to use hydrosilation technology to make alkoxylated silicone polymers, used as raw materials in this invention. These materials do not have the substantivity desired to make them suitable for use as fiber lubricants or antistats. It was not until the compounds of the present invention that the desirable lubrication and low volatility of silicone could be effectively used in a fiber lubricant system by incorporation of a phosphate group onto the polymer backbone, U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over other compounds, the efficiency and durability of the were not good enough to allow for cost effective incorporation of these materials in detergent formulations.

THE INVENTION

SUMMARY OF THE INVENTION

The present invention relates to a series of novel phosphated silicone polymers. These polymers have a terminal phosphate functional group present. The polymers by virtue of the pendent group deposit on fiber surfaces and form effective nonvolatile surface modifying finishes. The compounds of the present invention are substantive to cellulosic and synthetic fibers.

The compounds of this invention having a terminal phosphate group is represented by the following formula;

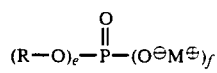

wherein
R is

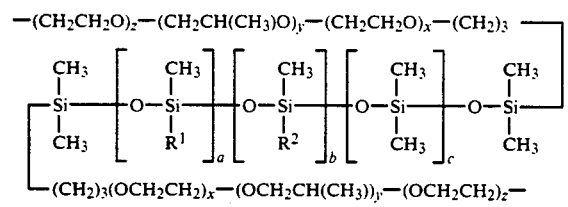

a is an integer from 0 to 200;
b is an integer from 0 to 200;
c is an integer from 1 to 200;
$R^1$ is selected from —$(CH_2)_n CH_3$ or phenyl;
n is an integer from 0 to 10;
$R^2$ is —$(CH_2)_3$—$(OCH_2CH_2)x$—$(OCH_2CH(CH_3))y$—$(OCH_2CH_2)z$—OH;
x, y and z are integers and are independently selected from 0 to 20;
e and f range from 1 to 2 with the proviso that e+f=3;
M is selected from H, Na, K, Li or $NH_4$.

The products of the present invention are prepared by reaction of a terminal hydroxyl containing silicone polymer with a suitable phosphating reagent.

One method of preparing the reactive hydroxyl containing silicone polymer is to react a silanic hydrogen containing polymer with allyl alcohol or allyl alcohol alkoxylate monomer. Procedures for this reaction are well known to those skilled in the art. U.S. Pat. No. 4,083,856 describes a suitable process.

EXAMPLES

Terminal Substituted Dimethicone Copolyol Compounds

Terminal substituted dimethicone copolyol compounds are well known and are marketed in the trade under many names.

The preferred method of placing this type of reactive hydroxyl group into the silicone polymer is by the reaction of terminal silanic hydrogen containing polymer with allyl alcohol alkoxylates. This technology is well known to those skilled in the art and are described in U.S. Pat. No. 4,083,856. These hydroxyl functional silicone compounds are subsequently phosphated.

Compounds suitable for use as reactants in the preparation of the compounds of the present invention conform to the following structure;

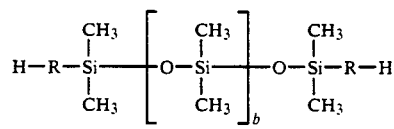

R is —$(CH2)_3$—O—$(CH_2CH_2$—O$)_x$—$(CH_2(CH_3)$-CH—O$)_y$—$(CH_2CH_2$—O$)_z$— x, y and z are integers independently ranging from 0 to 20;
b is an integer from 1 to 200.

These materials are available from Siltech Inc. Norcross Ga. and are marketed under the Siltech T series tradename.

| Name | x | y | z | Molecular Weight |
|---|---|---|---|---|
| Siltech T 710 | 0 | 0 | 0 | 1,000 |
| Siltech T 706 | 5 | 1 | 0 | 6,000 |
| Siltech T 710 | 2 | 1 | 1 | 10,000 |
| Siltech T 750 | 10 | 5 | 10 | 50,000 |
| Siltech T 790 | 20 | 20 | 20 | 86,000 |

PHOSPHATION

Phosphating Agents

Polyphosphoric Acid (PPA) is 115% phosphoric acid. When used as a phosphating agent it gives more mono ester than the phosphorus pentoxide.

Phosphorus pentoxide is $P_2O_5$. It is a more aggressive phosphating agent and produces more diester.

The silicone phosphates of this invention can be prepared by reacting the terminal hydroxyl containing silicone polymer with a suitable phosphating agent. Preferred phosphating reagents are polyphosphoric acid and phosphorus pentoxide.

The preparation of the novel silicone phosphates of this invention from the hydroxy silicone compounds can be illustrated by the following reaction in which R is the hydroxy silicone compound.

Phosphation Reaction Sequence

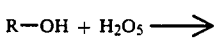

-continued $(R-O)-P(O)-(OH)_2$ and $(R-O-)_2P(O)-(OH)$

↓ Neutralization KOH/Water $(R-O)-P(O)-(OK)_2$ and $(R-O-)_2P(O)-(OK)$

It will be understood by the above reaction that the product of phosphation, whether using polyphosphoric acid or phosphorus pentoxide give a mixture of mono and di ester.

The following examples further illustrate the objects and advantages of this invention.

GENERAL PROCEDURE

The specified amount of hydroxy silicone compound (Siltech T series) is added to a suitable reaction vessel. The specified amount of either polyphosphoric acid or phosphorus pentoxide is changed to under good agitation over a 2 hr. period. The exothermic reaction raises the temperature of the mixture to about 70° C. After 1 hour slowly raise the temperature to 100° C. and hold 2-4 hours.

|  | Hydroxy Silicone | | Polyphosphoric Acid |
|---|---|---|---|
| Example | Name | Grams | Grams |
| 1 | Siltech T 710 | 1,000 | 56.5 |
| 2 | Siltech T 706 | 6,000 | 56.5 |
| 3 | Siltech T 710 | 10,000 | 56.5 |
| 4 | Siltech T 750 | 50,000 | 56.5 |
| 5 | Siltech T 790 | 90,000 | 56.5 |

|  | Phosphorus Pentoxide | | |
|---|---|---|---|
|  | Hydroxy Silicone | | Phosphorus Pentoxide |
| Example | Name | Grams | Grams |
| 6 | Siltech T 710 | 1,000 | 36.0 |
| 7 | Siltech T 706 | 6,000 | 36.0 |
| 8 | Siltech T 710 | 10,000 | 36.0 |
| 9 | Siltech T 750 | 50,000 | 36.0 |
| 10 | Siltech T 790 | 90,000 | 36.0 |

The compounds of examples 1-10 are neutralized to pH 7 with 20% aqueous base. The following bases are used; NaOH, KOH, LiOH, NH4OH.

| Example | Phosphated Silicone Example | Base Type |
|---|---|---|
| 11 | 1 | KOH |
| 12 | 2 | NaOH |
| 13 | 3 | LiOH |
| 14 | 4 | NH4OH |
| 15 | 5 | KOH |
| 16 | 6 | NaOH |
| 17 | 7 | KOH |
| 18 | 8 | NaOH |
| 19 | 9 | KOH |
| 20 | 10 | NaOH |
| 21 | 1 | KOH |
| 22 | 2 | NaOH |
| 23 | 3 | KOH |
| 24 | 4 | NaOH |
| 25 | 5 | NaOH |

APPLICATIONS EVALUATION

Lubrication

FRICTIONAL PROPERTIES

| | FRICTIONAL PROPERTIES | | |
|---|---|---|---|
| | | LUBRICATION DATA[1] | |
| | | Coefficient of Friction FIBER/METAL | |
| PRODUCT | DESCRIPTION (70 F.) | 100 (m/min.) | 300 (m/min.) |
| Butyl Stearate | White Liquid | 0.17 | 0.21 |
| Tridecyl Stearate | Clear Liquid | 0.25 | 0.27 |
| Example 16 | Clear Liquid | 0.11 | 0.11 |
| Example 10 | Clear Liquid | 0.10 | 0.19 |
| TMP Trioleate | Clear Amber Liquid | 0.25 | 0.35 |
| Ditridecyl adipate | Clear Amber Liquid | 0.28 | 0.29 |

[1]Rothchild F Meter. Fiber: 150 denier polyester. Temperature: 72 F., Relative humidity: 60%

What is claimed:

1. A silicone phosphate compound which is prepared by the phosphation reaction of;
   (a) a terminal hydroxyl group of a silicone polymer which conforms to the following structure;

$$H-R-\underset{\underset{CH_3}{|}}{\overset{\overset{CH_3}{|}}{Si}}-\left[O-\underset{\underset{CH_3}{|}}{\overset{\overset{CH_3}{|}}{Si}}\right]_b-O-\underset{\underset{CH_3}{|}}{\overset{\overset{CH_3}{|}}{Si}}-R-H$$

R is $-(CH_2)_3-O-(CH_2CH_2-O)_x-(CH_2(CH_3)-CH-O)_y-(CH_2CH_2-O)_z-$  x, y and z are integers independently ranging from 0 to 20;

b is an integer from 1 to 200; with
   (b) a phosphating agent selected from the group consisting of polyphosphoric acid and phosphorus pentoxide.

2. A compound of claim 1 wherein x is 0, y is 0 and z is 0.

3. A compound of claim 1 wherein x is 5, y is 1 and z is 0.

4. A compound of claim 1 wherein x is 2, y is 1 and z is 1.

5. A compound of claim 1 wherein x is 10, y is 5 and z is 10.

6. A compound of claim 1 wherein x is 20, y is 20 and z is 20.

* * * * *